(12) United States Patent
Aoyagi et al.

(10) Patent No.: US 6,869,284 B2
(45) Date of Patent: Mar. 22, 2005

(54) CAPSULE FOR DENTAL RESTORATION MATERIAL

(75) Inventors: Shuji Aoyagi, Tokyo (JP); Yoshimasa Suzuki, Tokyo (JP); Masaaki Kaneko, Tokyo (JP); Yoshihisa Mukasa, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 10/611,903

(22) Filed: Jul. 3, 2003

(65) Prior Publication Data

US 2004/0104133 A1 Jun. 3, 2004

Related U.S. Application Data

(63) Continuation of application No. 09/851,132, filed on May 9, 2001, now Pat. No. 6,682,347.

(30) Foreign Application Priority Data

May 31, 2000 (JP) ........................................ 2000-163408

(51) Int. Cl.[7] ................................................ A61C 5/04
(52) U.S. Cl. .......................................... 433/90; 604/218
(58) Field of Search ..................... 433/90, 89; 222/136; 206/63.5, 219; 604/218, 311

(56) References Cited

U.S. PATENT DOCUMENTS

| 2,754,590 A | 7/1956 | Cohen ........................... 433/90 |
|---|---|---|
| 3,028,052 A | 4/1962 | Archer ......................... 222/136 |
| 3,536,191 A | 10/1970 | Williams ....................... 206/47 |
| 3,648,899 A * | 3/1972 | Lukesch et al. ............... 222/82 |
| 3,684,136 A * | 8/1972 | Baumann ..................... 222/386 |
| 3,756,390 A | 9/1973 | Abbey et al. .................. 206/47 |
| 4,185,740 A | 1/1980 | Perfect ......................... 206/220 |
| 4,941,751 A * | 7/1990 | Muhlbauer ............... 366/182.1 |
| 5,026,283 A * | 6/1991 | Osanai et al. .................. 433/90 |
| 5,114,240 A | 5/1992 | Kindt-Larsen et al. ...... 366/129 |
| 5,275,312 A * | 1/1994 | Labruzzo ..................... 222/212 |
| 5,370,221 A | 12/1994 | Magnusson et al. ........ 206/221 |
| 5,531,255 A | 7/1996 | Vacca .......................... 141/285 |
| 6,135,771 A * | 10/2000 | Dragan et al. ................. 433/90 |
| 6,386,872 B1 | 5/2002 | Mukasa et al. ................ 433/90 |

FOREIGN PATENT DOCUMENTS

| EP | 0 397 589 | 11/1990 |
| GB | 463175 | 3/1937 |

* cited by examiner

*Primary Examiner*—John J. Wilson
(74) *Attorney, Agent, or Firm*—Oblon, Spivak, McClelland, Maier & Neustadt, P.C.

(57) ABSTRACT

A capsule for dental restoration material capable of administering, immediately after mixing, a mixture substantially free of air bubbles to a patient site to be restored is disclosed. The capsule comprises a dental restoration material comprising two components of definite amounts of previously weighed powder component and liquid component accommodated in a cylindrical mixing compartment in an isolated state from each other, and an air-permeable filter that does not allow the powder component to exit the mixing compartment, but can ventilate air within the mixing compartment into the outside of the mixing compartment.

10 Claims, 4 Drawing Sheets

CAPSULE FOR DENTAL RESTORATION MATERIAL

This application is a Continuation of application Ser. No. 09/851,132, filed on May 9, 2001 now U.S. Pat. No. 6,682,347, the contents of which are herein incorporated by reference. The entire disclosure of Japanese Patent Application No. 2000-163408 filed on May 31, 2000, including the specification, drawings, and abstract, is incorporated herein by reference in its entirety.

BACKGROUND OF THE INVENTION

1. Field of the Invention

The present invention relates to a capsule for dental restoration material, which can be administered to a site to be restored of a patient, immediately after mixing a dental restoration material comprising two components of definite amounts of previously weighed powder component and liquid component, for filling, cementing, lining and other applications for restoration of a tooth in the dental remedy field, and in a good state where the mixture does not substantially contain air bubbles.

2. Description of the Conventional Art

In general, a dental restoration material is used for restoration of a tooth, such as filling, cementing and lining. As the dental restoration material, a two-component system material comprising a powder component and a liquid component, which are reacted with each other upon mixing, is usually used. Hitherto, this two-component system dental restoration material was provided for use after appropriately weighing the powder component and the liquid component every time and mixing them with each other. However, in recent years, for the purposes of omitting a weighing operation of the powder component and the liquid component and an operation for accommodating the dental restoration material after mixing into a syringe for administering it to a site to be restored, there have been developed capsules for dental restoration material, in which definite amounts of the powder component and the liquid component are previously weighed and accommodated in an isolated state from each other, the isolated state is released at a desired time, the both components are mixed with each other by mechanical shaking in a mixer, and the resulting mixture is extruded and administered directly to a site to be restored, such as a tooth cavity, through a nozzle.

For example, in a capsule as disclosed in Japanese Patent Publication No. 38853/1991, a powder component of two components is accommodated in a mixing compartment of a capsule main body, and the other liquid component is charged in a bag (pillow) formed by a sheet film, which is assembled in a side portion of the mixing compartment accommodating the powder component by means of a clip. The capsule main body has an outlet hole in a front end portion thereof. This outlet hole can be clogged in a cylindrical bearing portion in a rear end portion of a nozzle. Further, the nozzle is kept from the outside by means of a separately formed cap, thereby preventing the powder component from leakage out of the mixing compartment. And, at the time of use, the clip is pushed toward a direction of the mixing compartment, thereby smashing and breaking the pillow accommodating the liquid component therein; the liquid component is made flow into an interior of the mixing compartment through an aperture provided on a side wall of the mixing compartment, followed by shaking in a mixer to mix the liquid component and the powder component with each other; the cylindrical bearing portion in the rear end portion of the nozzle is then rotated to release a passage of the nozzle; and a plunger is pushed by means of a push rod of a separately prepared applier to extrude the mixture through the nozzle.

Further, in a two-component system capsule for mixing and discharge as disclosed in Japanese Patent Laid-Open No. 268555/1987, a powder component of two components is accommodated in a mixing compartment within a capsule main body, and the other liquid component is accommodated in a bag (pillow) formed by a sheet film comprising a resin, a metal foil, or a laminate of a resin and a metal foil. In this pillow, the strength in the main body side is previously set to be low, and the pillow is assembled by a cap to be screw engaged with the capsule main body in the front end side of the capsule main body. At the time of use, when the cap is strongly screw engaged with the capsule main body and moved, the pillow is ruptured, the sheet in the capsule main body side is broken, and the liquid component flows into the mixing compartment through an outlet hole provided on a center axis of the front end of the capsule main body. Thus, when shaking is performed in a mixer, the liquid component is mixed with the powder component. After mixing, a through rod set within a nozzle provided on a center axis of the cap is pushed in and breaks through the sheet of the pillow in the cap side, i.e., in the nozzle side, to form a discharge outlet for the mixture. Thereafter, the through rod is removed, a plunger set in an interior of the rear end portion of the capsule main body is moved into the side of the front end portion of the capsule main body by a push rod of an applier, and the mixture in the mixing compartment is discharged through the nozzle.

Further, like Japanese Patent Laid-Open No. 268555/1987 as cited above, Japanese Patent Publication No. 81384/1991 discloses a capsule for dental restoration material in which a bag (pillow) having a liquid component accommodated therein, which is formed by a sheet film such as an aluminum foil, is aligned in an outside of a front end of a mixing compartment of a capsule main body; and the pillow is ruptured by a screw-in pushing pressure of a cap, thereby making the liquid component flow into the mixing compartment through an outlet hole on a center axis of the capsule main body. Thus, when shaking is performed in a mixer, the liquid component is mixed with the powder component. After mixing, a plunger having a pillow breakthrough body provided in a rear end portion of the capsule main body is moved by means of a push rod of an applier, to break through a front end of the pillow in the nozzle side, thereby extruding the mixture within the mixing compartment.

Each of the above-described capsules used a pillow in which the liquid component is wrapped by a sheet film using a metal foil or the like. As a capsule in a mode not using such a pillow, Japanese Patent Laid-Open No. 131459/1996 discloses a capsule having a structure comprising a cylindrical capsule main body having a mixing compartment for accommodating a powder component therein, in which a thin film-like seal portion for clogging a circular outlet hole for a mixture, which is provided on a center axis of a front end portion, is formed, a male screw is screw provided on an outer periphery side surface from a front end portion to a center portion, and an applier-engaging groove is engraved on an outer periphery side surface in the vicinity of a rear end portion; a cup-like liquid-accommodating tool for accommodating a liquid component therein, in which a thin film-like seal portion forming a circular flow-in hole for the liquid component is formed on a center axis of a front end portion thereof, an evagination portion that is embedded in a cylindrical portion for forming the mixing compartment of the capsule main body is provided on an outer periphery surface in the vicinity of the front end portion, and a convex stopper having a size such that it does not easily slide into the capsule main body during breaking through the thin film-like seal portion to form the flow-in hole for the liquid component, but, when a large force is applied, it is not inhibited to slide into the capsule main body, is provided on an outer side surface in the vicinity of a rear end portion thereof; a plunger, in which a tip portion thereof for breaking through the thin film-like seal portion of the liquid-accommodating tool and the thin film-like seal portion of the capsule main body has a planar rod-like protrusion in its front end portion, and an evagination portion that is embedded a cylindrical portion within the liquid-accommodating tool is provided on an outer side surface in the vicinity of the front end portion; a cap having a nozzle-engaging mouth on a center axis of a front end portion thereof and screw provided, on an inner periphery side surface thereof with a female screw to be screw engaged with the male screw that is screw provided on the capsule main body; and a nozzle having a shape such that a rear end portion thereof can be engaged with the outer surface of the front end portion of the capsule main body.

In the capsules having such various structures, when the dental restoration material comprising two components of definite amounts of the previously weighed powder component and liquid component as is mixed by shaking in a mixer, air present in the mixing compartment mingles into the mixture, whereby it exists as air bubbles. For this reason, the dental restoration material administered in a dental restoration site such as a cavity of a patient contains the air bubbles. Accordingly, the capsules of the conventional art involved various problems including a decrease in the strength and a change in the color tone with respect to the dental restoration material.

SUMMARY OF THE INVENTION

An object of the present invention is to overcome the above-described problems of the capsules for dental restoration material of the conventional art and provide a capsule for dental restoration material, which is free from the occurrence of a phenomenon wherein, when a dental restoration material comprising two components of definite amounts of previously weighed powder component and liquid component accommodated in a capsule for dental restoration material of the conventional art is mixed by shaking in a mixer, air present in a mixing compartment mingles as air bubbles into the mixture.

In order to achieve the above-described object, we, the present inventors made extensive and intensive investigations. As a result, it has been found that in a capsule for dental restoration material for directly administering to a restoration site of a tooth with a mixture prepared by subjecting a dental restoration material comprising two components of definite amounts of previously weighed powder component and liquid component accommodated in a cylindrical mixing compartment in an isolated state from each other to making the liquid component flow into the mixing compartment and mixing the both components, when an air-permeable filter that does not pass the powder component therethrough but can ventilate air within the mixing compartment into the outside of the mixing compartment is placed in at least a part of a peripheral wall of the mixing compartment, the capsule for dental restoration material is placed in a vacuum atmosphere before mixing the powder component and the liquid component, whereby the air within the mixing compartment can be sucked into the outside of the mixing compartment, leading to accomplishment of the invention.

Further, it has also been found that the air-permeable filter may be placed in at least one of a state where it is placed so as to clog a passage for the mixture, which connects a nozzle for directly administering the mixture to the restoration site of the tooth to the mixing compartment, a state where it is placed on a side wall of the mixing compartment, and a state where it is placed in a plunger extruding the mixture toward the nozzle for directly administering the mixture within the mixing compartment to the restoration site of the tooth; and that it is preferred that the air-permeable filter has a characteristic that an air flow rate is 0.1 to 1,000 L/min·cm$^2$ in the case where the ventilation is carried out under the conditions that a pore size is 0.1 to 100 $\mu$m, a thickness is 50 to 1,000 $\mu$m, and a differential pressure of air at 25° C. is 69 kPa.

DESCRIPTION OF THE PREFERRED EMBODIMENTS

Embodiments of the capsule for dental restoration material according to the present invention will be described in detail with reference to the drawings.

Figure 1:
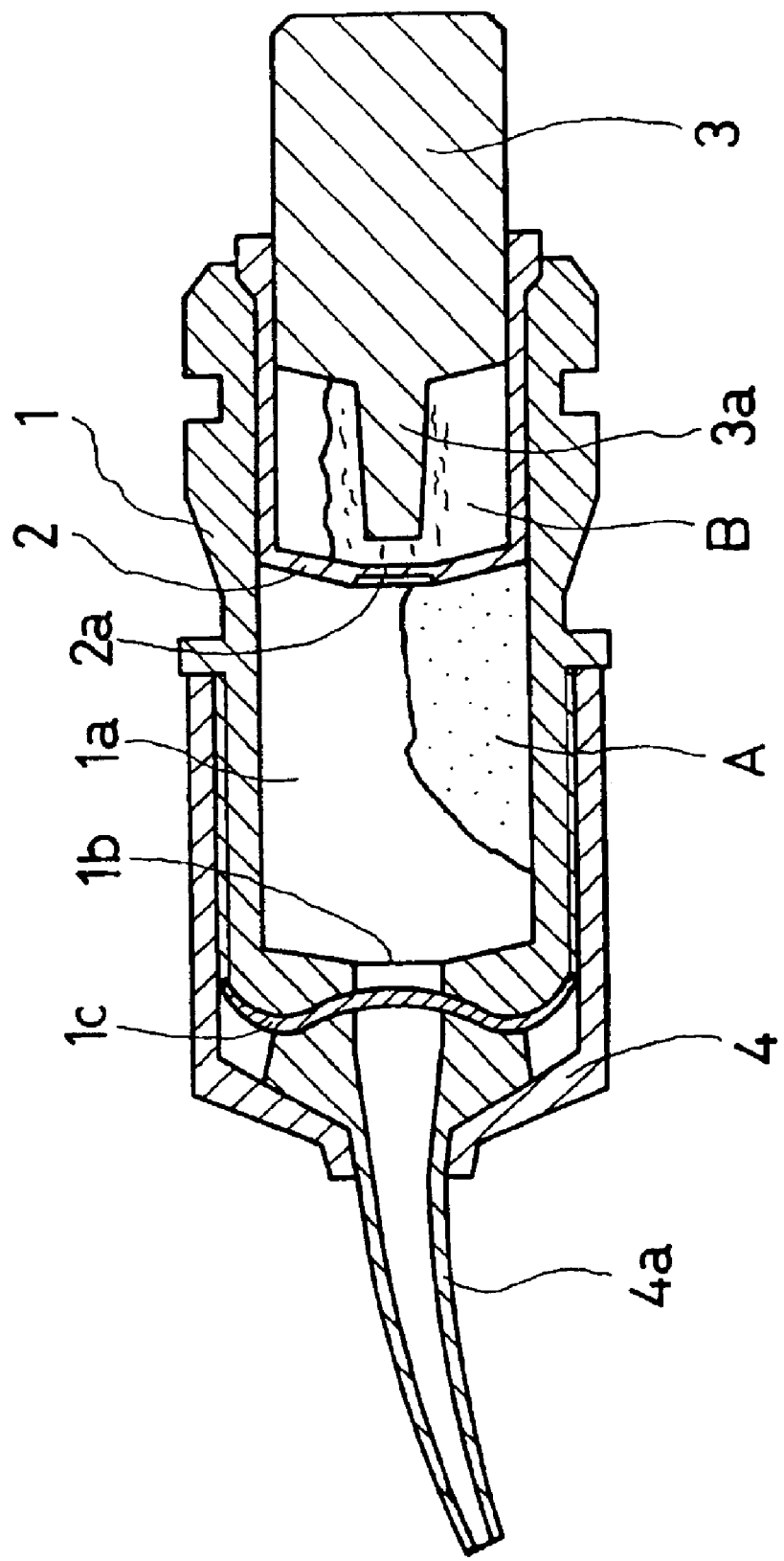
FIG. 1 is an explanatory side cross-sectional view of one embodiment of a capsule for dental restoration material according to the present invention.
Figure 2:
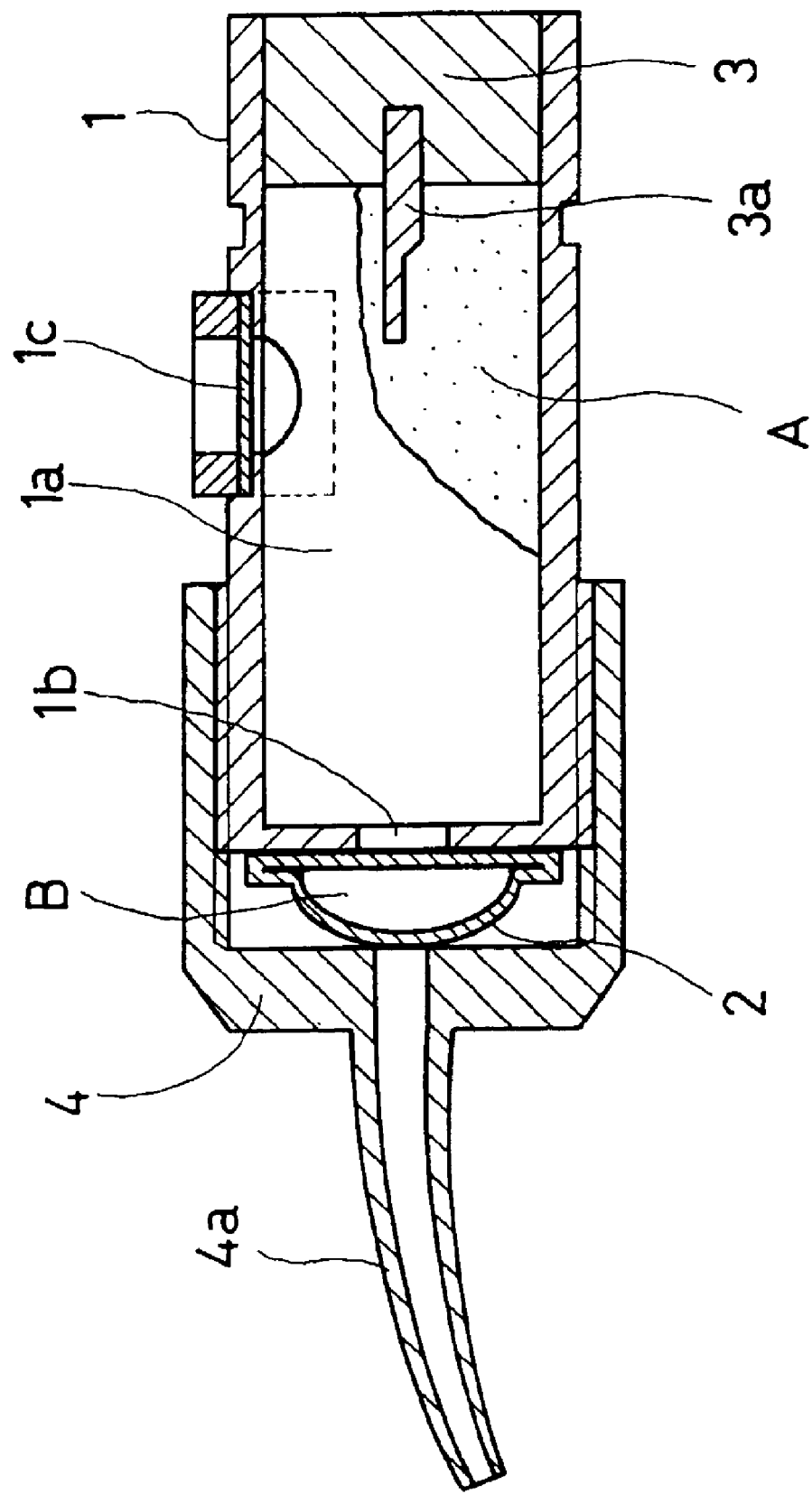
FIG. 2 is an explanatory side cross-sectional view of another embodiment of a capsule for dental restoration material according to the present invention.
Figure 3:
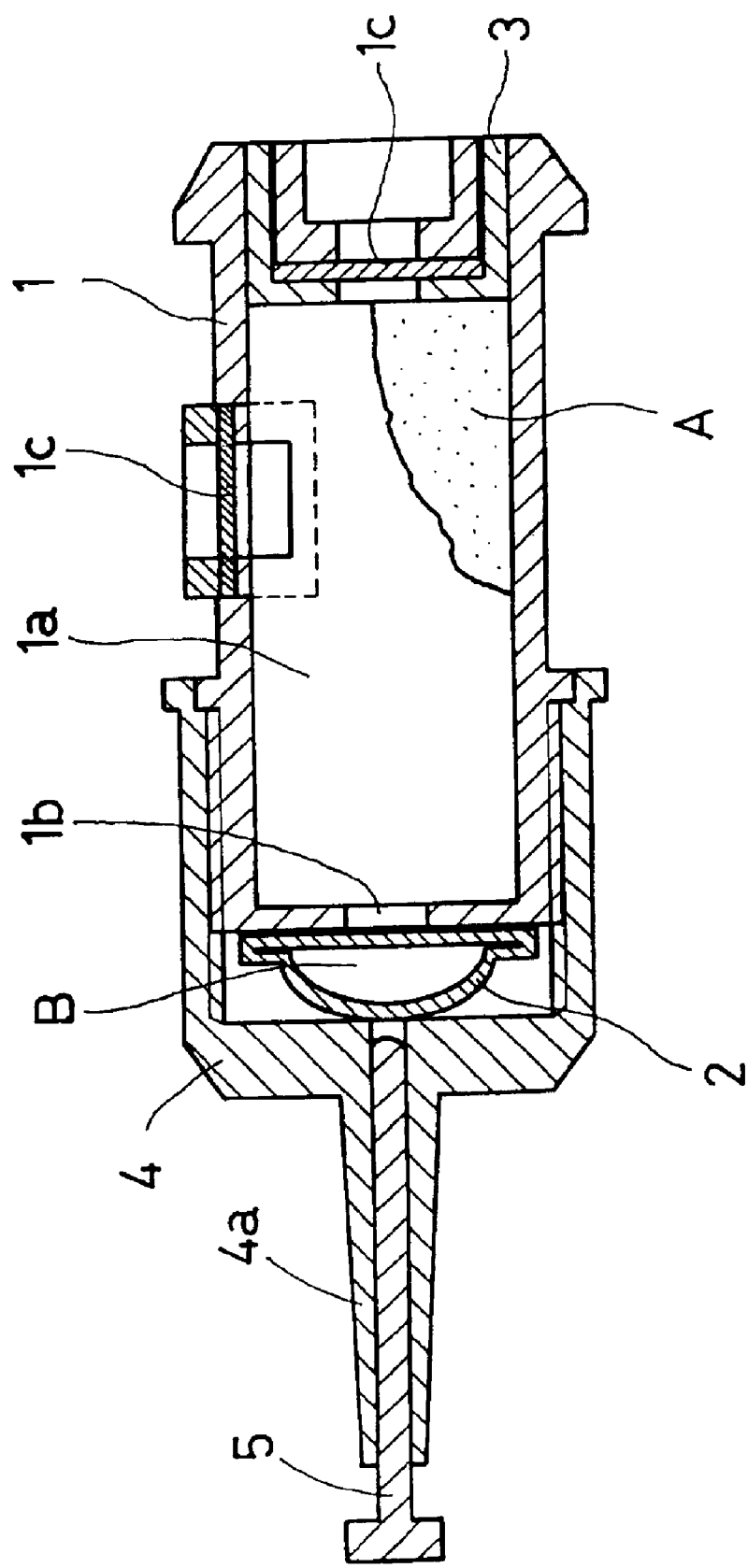
FIG. 3 is an explanatory side cross-sectional view of a still another embodiment of a capsule for dental restoration material according to the present invention.
Figure 4:
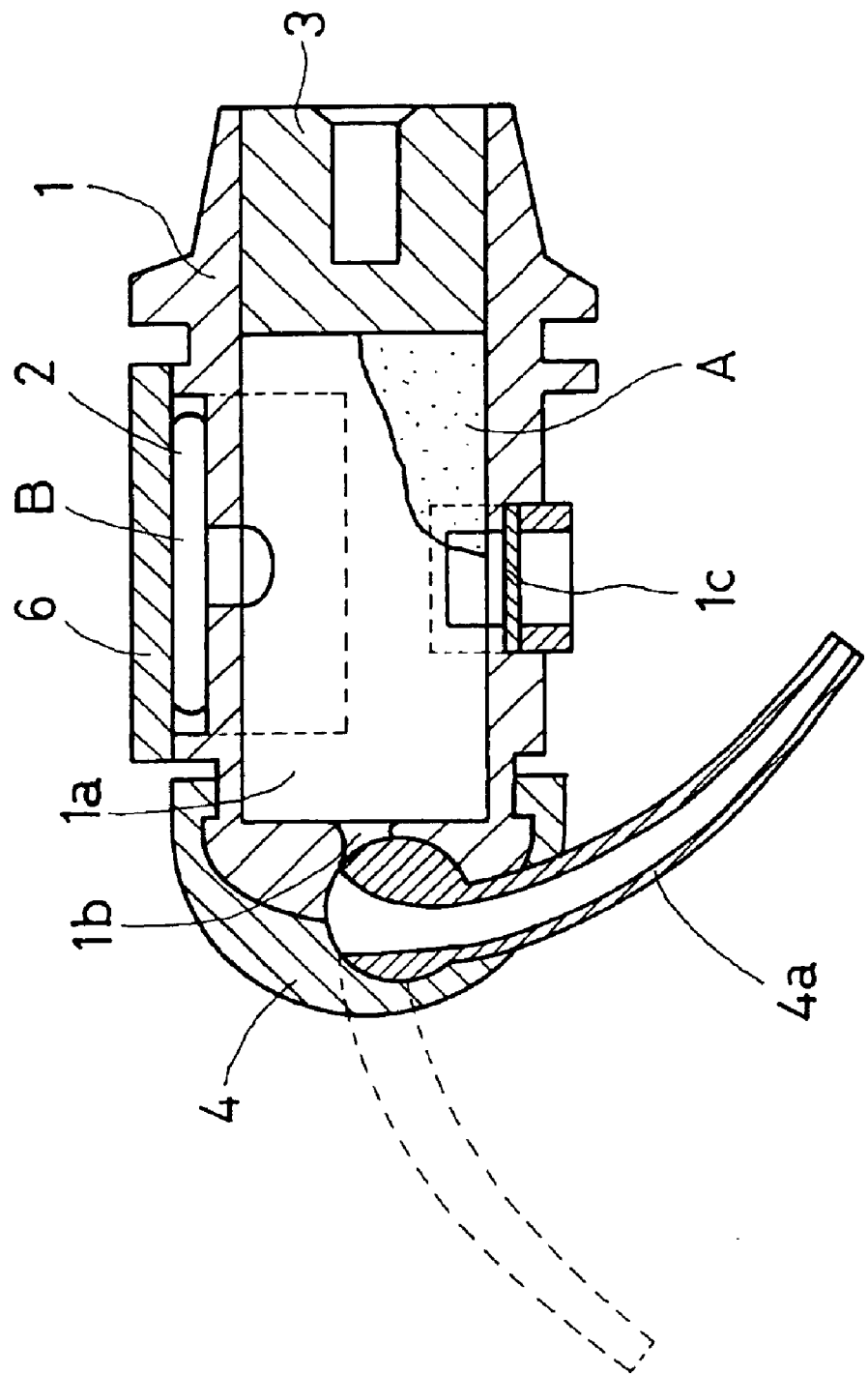
FIG. 4 is an explanatory side cross-sectional view of a still other embodiment of a capsule for dental restoration material according to the present invention.

FIG. 1 is an explanatory side cross-sectional view of one embodiment of a capsule for dental restoration material according to the present invention; FIG. 2 is an explanatory side cross-sectional view of another embodiment of a capsule for dental restoration material according to the present invention; FIG. 3 is an explanatory side cross-sectional view of a still another embodiment of a capsule for dental restoration material according to the present invention; and FIG. 4 is an explanatory side cross-sectional view of a still other embodiment of a capsule for dental restoration material according to the present invention.

In the drawings, a numeral 1 is a monolithically formed synthetic resin-made cylindrical capsule main body, in which a definite amount of a previously weighed powder component A is accommodated and which is provided with a cylindrical mixing compartment 1a for mixing the powder component A with a liquid component B when the liquid component B flows thereinto. The capsule main body 1 is also provided with an outlet hole 1b for a mixture comprising the powder component A and the liquid component B mixed with each other on a center axis in a front end portion thereof. Each of the embodiments as shown in the drawings has a shape such that a cap 4 provided with a nozzle 4a as described later on an outer surface of the front end portion, or a cap 4 supporting the nozzle 4a together with the capsule main body 1, can be fixed (a male screw in the embodiments shown in FIGS. 1 to 3 and an engagement concave in the embodiment shown in FIG. 4, respectively).

A numeral 2 is a liquid-accommodating tool for accommodating a definite amount of the previously weighed liquid component B. In the embodiment shown in FIG. 1, the liquid-accommodating tool 2 is a integrally formed synthetic resin-made cylindrical cup that can slide toward the side of the outlet hole 1*b* for the mixture within the cylindrical mixing compartment 1*a* of the capsule main body 1 and is provided with a thin film-like seal portion 2*a* to form a circular flow-in hole for the liquid component B on a center axis in a front end portion thereof. In the embodiments shown in FIGS. 2 and 3, the liquid-accommodating tool 2 is constituted by a bag (pillow) in which the liquid component B is wrapped by a sheet film made by a resin, a metal foil, or a laminate of a resin and a metal foil, to be installed between the capsule main body 1 and the cap 4 provided with the nozzle 4*a*. In the embodiment shown in FIG. 4, the liquid-accommodating tool 2 is constituted by a bag (pillow) in which the liquid component B is wrapped by a sheet film made by a resin, a metal foil, or a laminate of a resin and a metal foil, to be installed in the outside of an aperture hole provided on the side surface of the capsule main body 1.

A numeral 3 is a synthetic resin-made plunger for extruding the mixture of the powder component A and the liquid component B mixed with each other within the mixing compartment 1*a* of the capsule main body 1 toward the side of the outlet hole 1*b* for the mixture. The embodiment shown in FIG. 1 is an embodiment in which the plunger 3 is a integrally formed synthetic resin-made one that can slide toward the side of the thin film-like seal portion 2*a* within the liquid-accommodating tool 2, a rod-like protrusion 3*a* breaking through the thin film-like seal portion 2*a* of the liquid-accommodating tool 2 is provided in a front end portion thereof, and after making the liquid component B within the liquid-accommodating tool 2 flow into the mixing compartment 1*a* of the capsule main body 1, the plunger 3 moves together with the liquid-accommodating tool 2, thereby inserting the rod-like protrusion 3*a* into the outlet hole 1*b* for the mixture of the capsule main body 1. The embodiments shown in FIGS. 2 to 4 are an embodiment in which the plunger 3 is a monolithically formed synthetic resin-made one having such a shape that the mixture can slide toward the side of the outlet hole 1*b* for the mixture within the mixing compartment 1*a* of the capsule main body 1. In the embodiment shown in FIG. 2, the plunger 3 is provided with the rod-like protrusion 3*a* breaking through the sheet film in the opposite side to the outlet hole 1*b* of the liquid-accommodating tool 2 in the front end portion thereof.

A numeral 4 is a synthetic resin-made cap having such a shape that it can be fixed to an outer surface of the front end portion of the capsule main body 1 for disposing the nozzle 4*a* in the front end portion of the capsule main body 1 (a male screw in the embodiments shown in FIGS. 1 to 3 and an engagement protrusion in the embodiment shown in FIG. 4, respectively). The cap 4 includes the embodiments shown in FIGS. 1 and 4 in which when the cap 4 is fixed to the outer surface of the front end portion of the capsule main body 1, it supports the nozzle 4*a* between the cap 4 and the capsule main body 1 and those shown in FIGS. 2 and 3 in which the nozzle 4*a* is formed monolithically with the cap 4. Further, there is another embodiment not shown in the drawings, in which it is not necessary that the liquid-accommodating tool 2 is disposed facing at the outlet hole 1*b* of the capsule main body 1, as in the embodiments shown in FIGS. 1 and 4 and in which in the case where the nozzle 4*a* is not rotated, the cap 4 is omitted, whereby the nozzle 4*a* is fixed to the capsule main body 1 by screw engagement or embedding.

In the case where the liquid-accommodating tool 2 is a capsule comprising a bag (pillow) containing the liquid component B wrapped by the sheet film as in the embodiment shown in FIG. 3, a numeral 5 is a through rod previously set within the nozzle 4*a* provided on a center axis of the cap 4, such that it breaks through the sheet film in the opposite side to the outlet hole 1*b* of the liquid-accommodating tool 2, thereby enabling to supply the mixture of the powder component A and the liquid component B mixed within the mixing compartment 1*a* of the capsule main body 1 into the nozzle 4*a*.

In the case where the liquid-accommodating tool 2 is a capsule comprising a bag (pillow) containing the liquid component B wrapped by the sheet film as in the embodiment shown in FIG. 4, a numeral 6 is a clip installing the liquid-accommodating tool 2 in an outer portion of the side wall of the mixing compartment 1*a* of the capsule main body 1. During the use, the clip 6 is pushed toward the direction of the mixing compartment 1*a* to smash and break the sheet film of the liquid-accommodating tool 2 having the liquid component B accommodated therein, thereby enabling to supply the liquid component B into the mixing compartment 1*a* of the capsule main body 1.

In the capsules for dental restoration material having such various shapes, the capsule for dental restoration material according to the present invention is characterized by providing an air-permeable filter 1*c* that does not pass the powder component A therethrough but can ventilate air within the mixing compartment 1*a* into the outside of the mixing compartment 1*a* in at least a part of a peripheral wall of the cylindrical mixing compartment 1*a* of the capsule main body 1.

In the embodiment shown in FIG. 1, the air-permeable filter 1*c* is placed in a state of clogging a mixture passage connecting the nozzle 4*a* for directly administering the mixture to a restoration site of a tooth to the mixing compartment 1*a*; in the embodiments shown in FIGS. 2 and 4, the air-permeable filter 1*c* is placed on the side wall of the mixing compartment 1*a*; and in the embodiment shown in FIG. 3, the air-permeable filter 1*c* is placed on the side wall of the mixing compartment 1*a* and the plunger 3 extruding the mixture within the mixing compartment 1*a* toward the nozzle 4*a* for directly administering it to a dental restoration site of a tooth. In order to place the air-permeable filter 1*c* in at least a part of the peripheral wall of the cylindrical mixing compartment 1*a* of the capsule main body 1, it is necessary to fix the air-permeable filter 1*c* along the peripheral wall of the cylindrical mixing compartment 1*a* of the capsule main body 1. Accordingly, in other cases than the case where the air-permeable filter 1*c* is kept between the capsule main body 1 and the cap 4 so as to clog the outlet hole 1*b* of the capsule main body 1 as in the embodiment shown in FIG. 1, an aperture window is formed on the side wall of the cylindrical mixing compartment 1*a* of the capsule main body 1 or on the plunger 3 in the side facing at the mixing compartment 1*a*, and the air-permeable filter 1*c* disposed in this aperture window is pressed and fixed with a presser that is similarly provided with an aperture window. Further, the air-permeable filter 1*c* may be provided upon fixing to an inner side wall of the mixing compartment 1*a* with an adhesive, etc. In this case, it is preferred that the air-permeable filter 1*c* is provided in a position other than the inner side wall of the mixing compartment 1*a* constituting a sliding surface with the plunger 3 (the liquid-accommodating tool 2 in the case of the embodiment shown in FIG. 1) that slides and moves within the mixing compartment 1*a*.

It is preferred that the air-permeable filter 1c has a characteristic that an air flow rate is 0.1 to 1,000 L/min·cm² in the case where the ventilation is carried out under the conditions that a pore size is 0.1 to 100 μm, a thickness is 50 to 1,000 μm, and a differential pressure of air at 25° C. is 69 kPa. This is because the powder component A accommodated within the cylindrical mixing compartment 1a of the capsule main body 1 does not leak out of the mixing compartment 1a during the transportation or keeping; when the capsule for dental restoration material is installed in a capsule-installing compartment of the mixer and the capsule-installing compartment is made vacuum, the mixing compartment 1a can be made to a desired degree of vacuum within a few seconds; and the air-permeable filter 1c may be broken through with the rod-like protrusion 3a of the plunger 3 as in the embodiment shown in FIG. 1.

Usually, a powder component for dental restoration material has a grain size of 50 μm or less, and a liquid component B for dental restoration material has a relatively high viscosity of 220 to 750 cP as measured under the temperature condition of 23° C. using a B type rotational viscometer. Accordingly, a material which does not pass the powder component A therethrough does not inevitably pass the liquid component B therethrough. Examples of materials that can be used suitably for the air-permeable filter 1c having such a characteristic, include fabric materials textured with fibers such as cellulose fibers, glass fibers, polyethylene fluoride fibers, silicone fibers, and silica fibers; and film-like materials made of nylon, polyester, polyethylene, polypropylene, polycarbonate, polyether sulfone, or a mixture thereof.

Next, a method for use of the capsule for dental restoration material according to the present invention, which comprises the above-described construction, will be described below.

First of all, the liquid component B within the liquid-accommodating tool 2 is made flow into the mixing compartment 1a of the capsule main body 1. In the embodiment shown in FIG. 1, the plunger 3 is made slide toward the side of the outlet hole 1b of the capsule main body 1, thereby breaking through the thin film-like seal portion 2a forming the flow-in hole for the liquid component B provided on the center axis of the front end portion of the liquid-accommodating tool 2. In the embodiments shown in FIGS. 2 and 3, the capsule main body 1 is moved toward the side of the cap 4, thereby rupturing and breaking a portion of the side of the outlet hole 1b of the sheet film comprising a resin, a metal foil, or a laminate of a resin and a metal foil, of the liquid-accommodating tool 2 installed between the capsule main body 1 and the cap 4 provided with the nozzle 4a. In the embodiment shown in FIG. 4, the sheet film comprising a resin, a metal foil, or a laminate of a resin and a metal foil, of the liquid-accommodating tool 2 installed with the clip in the outside of the aperture hole provided on the side surface of the capsule main body 1 is ruptured and broken by pushing the clip toward the direction of the mixing compartment 1a.

Thereafter, this capsule for dental restoration material is installed separately in a capsule-installing compartment of an exclusive mixer (not shown); the capsule-installing compartment is made vacuum, thereby sucking air within the mixing compartment 1a into the outside of the mixing compartment 1a via the air-permeable filter 1c placed in at least a part of the peripheral wall of the cylindrical mixing compartment 1a of the capsule main body 1; and the powder component A and the liquid component B are then mixed with each other by shaking in the mixer, to obtain a mixture where no air bubbles are present.

After mixing of the powder component A and the liquid component B has been completed, the capsule for dental restoration material is taken out from the mixer and is installed separately in an exclusive applier (not shown), and the plunger 3 is moved toward the side of the outlet hole 1b of the capsule main body 1 by means of a push rod of the applier. At this time, in the embodiment shown in FIG. 3, a portion in the opposite side to the outlet hole 1b of the sheet film comprising a resin, a metal foil, or a laminate of a resin and a metal foil, of the liquid-accommodating tool 2 is broken through by means of the through rod 5 set within the nozzle 4a provided on the center axis of the cap 4, and the through rod 5 is then taken out from the nozzle 4a. Further, in the embodiment shown in FIG. 4, the nozzle 4a is rotated to a position shown by a broken line, thereby connecting the outlet hole 1b of the capsule main body 1 to the nozzle 4a.

Thus, when the plunger 3 is moved toward the side of the outlet hole 1b of the capsule main body 1 by pushing with the push rod of the applier, the mixture within the mixing compartment 1a of the capsule main body 1 is extruded toward the outlet hole 1b of the capsule main body 1 in a state that no air bubbles are present and administered to a restoration site of a tooth from the nozzle 4a. In this case, in the embodiment shown in FIG. 1, the rod-like protrusion 3a of the plunger 3 penetrates through the outlet hole 1b of the capsule main body 1 and breaks through the air-permeable filter 1c installed between the capsule main body 1 and the cap 4 provided with the nozzle 4a. Further, in the embodiment shown in FIG. 2, when the rod-like protrusion 3a of the plunger 3 penetrates through the outlet hole 1b of the capsule main body 1 and breaks through a portion in the opposite side to the outlet hole 1b of the sheet film comprising a resin, a metal foil, or a laminate of a resin and a metal foil, of the liquid-accommodating tool 2 installed between the capsule main body 1 and the cap 4 provided with the nozzle 4a, the mixture is administered to a restoration site of a tooth from the nozzle 4a.

As described above in detail, with respect to the capsule for dental restoration material according to the present invention, in a capsule for dental restoration material for directly administering a dental restoration site of a tooth with a mixture prepared by subjecting a dental restoration material comprising two components of definite amounts of previously weighed powder component and liquid component accommodated in a cylindrical mixing compartment in an isolated state from each other to making the liquid component flow into the mixing compartment and mixing the both components, an air-permeable filter that does not pass the powder component therethrough but can ventilate air within the mixing compartment into the outside of the mixing compartment is placed in at least a part of a peripheral wall of the mixing compartment. Accordingly, when the mixing compartment is made vacuum in a mixer, prior to mixing the dental restoration material comprising two components of definite amounts of the previously weighed powder component and liquid component, and shaking is performed to effect mixing the dental restoration material, the dental restoration material in a good state that no air bubbles are present in the mixture can be administered directly to a restoration site such as a cavity of a tooth in a simple operation of setting in an applier and extrusion.

Further, this air-permeable filter may be placed in at least one of a state where it is placed so as to clog a passage for the mixture, which connects a nozzle for directly administering the mixture to the restoration site of the tooth to the mixing compartment, a state where it is placed on a side wall of the mixing compartment, and a state where it is placed in a plunger extruding the mixture toward the nozzle for directly administering the mixture within the mixing compartment to the restoration site of the tooth. Accordingly, the air-permeable filter can be thoroughly applied to various structures of the capsule main body.

Still further, when the air-permeable filter has a characteristic that an air flow rate is 0.1 to 1,000 L/min·cm$^2$, in the case where the ventilation is carried out under the conditions that a pore size is 0.1 to 100 μm, a thickness is 50 to 1,000 μm, and a differential pressure of air at 25° C. is 69 kPa, not only the mixing compartment within the capsule main body can be easily made vacuum, but also the powder component within the mixing compartment of the capsule main body is free from leakage from the air-permeable filter.

In the light of the above, the capsule for dental restoration material according to the present invention, which possesses various advantages, is greatly valuable in contributing to the dental field.

While the invention has been described in detail and with reference to specific embodiments thereof, it will be apparent to one skilled in the art that various changes and modifications can be made therein without departing from the spirit and scope thereof.

What is claimed:

1. A capsule for dental restoration material for directly administering to a tooth a mixture of a powder and liquid, comprising:
    a main body, containing the powder, having inner surfaces defining a cylindrical mixing compartment and outlet hole,
    a liquid accommodating tool having a seal, configured to accommodate the liquid and to move in the compartment toward the outlet hole,
    a plunger comprising a protrusion movably held in the liquid accommodating tool, the plunger being movable in the liquid accommodating tool such that protrusion breaks the seal in the liquid accommodating tool causing the powder and the liquid to mix within the mixing compartment and breaks through an air-permeable filter forcing the mixture toward the outlet hole; and
    said air-permeable filter being configured to seal the powder within the mixing compartment, being located in a passage for the mixture connecting a nozzle to the mixing compartment, and being configured to allow air to escape from the mixing compartment through the nozzle.

2. The capsule of claim 1, wherein an air flow rate per unit area through the air-permeable filter varies from 0.1 to 1000 L/(min cm$^2$).

3. The capsule of claim 1, wherein a pore size of the air-permeable filter varies from 0.1 to 100 μm.

4. The capsule of claim 1, wherein a thickness of the air-permeable filter varies from 50 to 1000 μm.

5. The capsule of claim 1, wherein a differential air pressure across the air-permeable filter is approximately 69 kPa at a temperature of approximately 25° C.

6. The capsule of claim 1, wherein the air-permeable filter is made of a fabric material.

7. The capsule of claim 6, wherein the fabric material is cellulose, glass, polyethylene fluoride, silicone, or silica fibers.

8. The capsule of claim 1, wherein the air-permeable filter is made of a film material.

9. The capsule of claim 8, wherein the film material is made of nylon, polyester, polyethylene, polypropylene, polycarbonate, polyether sulfone, or a mixture thereof.

10. The capsule of claim 1, wherein a mixing within the mixing compartment takes place in a vacuum.

* * * * *

UNITED STATES PATENT AND TRADEMARK OFFICE
CERTIFICATE OF CORRECTION

PATENT NO. : 6,869,284 B2
DATED : March 22, 2005
INVENTOR(S) : Aoyagi et al.

It is certified that error appears in the above-identified patent and that said Letters Patent is hereby corrected as shown below:

Title page,
Items [45] and [*] Notice, should read as follows:
-- [45] **Date of Patent: *Mar. 22, 2005**

[*] Notice: Subject to any disclaimer, the term of this patent is extended or adjusted under 35 U.S.C. 154(b) by 0 days.

This Patent is subject to a terminal disclaimer. --

Signed and Sealed this

Twenty-fourth Day of May, 2005

JON W. DUDAS
*Director of the United States Patent and Trademark Office*